United States Patent
Sheridan (10) Patent No.: US 7,415,982 B1
(45) Date of Patent: Aug. 26, 2008

(54) SMOKELESS PIPE

(76) Inventor: Timothy B. Sheridan, 119 W. Mount Airy Ave., Philadelphia, PA (US) 19119

( * ) Notice: Subject to any disclaimer, the term of this patent is extended or adjusted under 35 U.S.C. 154(b) by 0 days.

(21) Appl. No.: 09/783,811

(22) Filed: Feb. 15, 2001

(51) Int. Cl.
*A24F 1/28* (2006.01)
*A24F 1/22* (2006.01)

(52) U.S. Cl. .................... 131/191; 131/194; 131/198.1; 131/197

(58) Field of Classification Search ................ 131/330, 131/194, 180, 184, 183, 271, 191, 178, 179, 131/199, 225, 195.1; 128/202.21
See application file for complete search history.

(56) References Cited

U.S. PATENT DOCUMENTS

| | | | | |
|---|---|---|---|---|
| 201,031 A * | 3/1878 | McCarter | ................... | 131/182 |
| 239,196 A * | 3/1881 | Rousseaux | ............ | 128/202.21 |
| 1,591,743 A * | 7/1926 | Chance | ........................ | 131/174 |
| 2,057,353 A | 10/1936 | Whittemore, Jr. | | |
| 2,191,672 A * | 2/1940 | Malicki | ........................ | 131/182 |
| 2,318,639 A * | 5/1943 | Sibert | .......................... | 131/194 |
| 2,594,680 A * | 4/1952 | Rehfeld | ....................... | 131/174 |
| 2,860,638 A * | 11/1958 | Bartolomeo | ........... | 128/202.21 |
| 3,170,468 A * | 2/1965 | Smith | .......................... | 131/194 |
| 3,318,315 A * | 5/1967 | Orter | ........................... | 131/173 |
| 3,410,273 A * | 11/1968 | Bolles | ........................ | 131/271 |
| 4,119,335 A * | 10/1978 | Rieffle et al. | ................ | 285/249 |
| 4,141,369 A | 2/1979 | Burruss | | |
| 4,289,149 A * | 9/1981 | Kyriakou | .................... | 131/175 |
| 4,303,083 A | 12/1981 | Burruss, Jr. | | |
| 4,328,795 A * | 5/1982 | Cabaniss, III | ............... | 131/180 |
| 4,735,217 A | 4/1988 | Gerth et al. | | |
| 4,756,318 A | 7/1988 | Clearman et al. | | |
| 4,848,374 A | 7/1989 | Chard et al. | | |
| 4,947,874 A | 8/1990 | Brooks et al. | | |
| 5,188,401 A * | 2/1993 | Staniforth | ................... | 285/249 |
| 5,564,442 A | 10/1996 | MacDonald et al. | | |
| 5,687,746 A * | 11/1997 | Rose et al. | ............. | 128/202.21 |
| 5,944,025 A | 8/1999 | Cook et al. | | |
| 6,095,153 A | 8/2000 | Kessler et al. | | |
| 6,148,826 A * | 11/2000 | Lancaster et al. | ........... | 131/191 |
| 6,260,554 B1 * | 7/2001 | Rowland et al. | ............ | 131/173 |
| 6,318,376 B1 * | 11/2001 | Cheng | ........................ | 131/173 |

* cited by examiner

*Primary Examiner*—Steven P. Griffin
*Assistant Examiner*—Carlos Lopez
(74) *Attorney, Agent, or Firm*—Caesar, Rivise, Bernstein, Cohen & Pokotilow, Ltd.

(57) ABSTRACT

A smokeless pipe for the ingestion of tobacco products which includes an elongated hollow member having a proximal end, a distal end, and a length therebetween. The elongated hollow member includes a constricted portion along its length to retain the tobacco products within, a first opening to enable a user to draw from, a fill port to enable a user to fill the hollow member with the tobacco products, and a bulbous chamber.

9 Claims, 10 Drawing Sheets

SMOKELESS PIPE

FIELD OF THE INVENTION

This invention relates generally to a smokeless pipe, and more specifically to a smokeless pipe that utilizes a combination of heat generated from a conventional butane lighter and an airstream to provide a noncombustible and nonpyrolytic method for heating and inhaling the active volatile compounds and components of tobacco or other smoking materials without the ingestion of toxic and carcinogenic compounds.

BACKGROUND OF THE INVENTION

The term smoking material is intended to include any combustible organic material containing volatile ingredients which upon combustion are vaporized and can be drawn into the mouth and respiratory passages of a smoker. Such materials include tobacco, licorice, eucalyptus, teas, flower petals, and other herbs. Such smoking materials may be used alone or in various combinations with one another. The traditional methods of tobacco smoking are based on the combustion of the tobacco, which causes the vaporization of volatile components. The well-known disadvantage of such traditional methods of tobacco utilization is that the smoker not only inhales the desired taste and other volatile active ingredients, but also inhales the combustion by-products which are associated with cancer and diseases of the heart and lungs. Such products and by-products of combustion include carbon monoxide, benzo(a)pyrene, volatilized cadmium, nitrogen oxides, sulfur oxides, hydrogen sulfide, and a spectrum of heavy hydrocarbons which are either the direct result of combustion of organic material or are the result of the unnecessarily-high-temperature volatilization of ingredients in the unburned portion of the smoking material immediately adjacent to the combustion zone.

Previous inventions and methods related to the use of smoking materials have sought to eliminate the combustion products from the desirable gaseous ingredients. For example, U.S. Pat. No. 4,947,874 (Brooks et al.) discloses smoking articles that employ an electrical resistance heating element to provide a tobacco-flavored smoke or aerosol and other sensations of smoking without burning tobacco or other substances and without producing any combustion or pyrolysis products including carbon monoxide or any sidestream smoke or odor.

U.S. Pat. No. 4,848,374 (Chard et al.) also discloses a smoking device wherein loss of nicotine to the smoker by pyrolysis and in sidestream smoke is substantially avoided.

U.S. Pat. No. 4,756,318 (Clearman et al.) discloses a smoking article with a tobacco jacket. In several embodiments described in this patent, tobacco does not burn but still provides tobacco flavors to the aerosol delivered to the user.

U.S. Pat. No. 4,141,369 (Burruss) discloses an electrical device for the noncombustion utilization of tobacco and other smoking materials. The device consists of a canister or other appropriate container within which air is electrically heated to an appropriate temperature for volatilizing the desired components of smoking material previously inserted into a receptacle provided in the mouthpiece part of the invention.

U.S. Pat. No. 6,095,153 (Kessler et al.) discloses a device that vaporizes volatile materials while avoiding combustion and denaturation of materials which provides an alternative to combustion as a means of volatilizing bioactive and flavor compounds to make such flavor compounds available for inhalation without generating toxic or carcinogenic substances that are byproducts of combustion and pyrolysis.

While the aforementioned prior art devices have solved some of the problems associated with providing a noncombustible and nonpyrolytic method for heating and inhaling the active volatile compounds and components of tobacco and of other smoking materials without the ingestion of toxic and carcinogenic compounds, there exists a need for a simple and easy method of inhaling the active volatile compounds and components of smoking materials without the ingestion of toxic and carcinogenic compounds.

More specifically, this invention teaches a smokeless pipe in the form of an elongated hollow member that includes an open stem at one end for a user to draw upon and a bulbous chamber at the opposite end that includes a plurality of vent holes spaced equidistantly which enable cool air to mix with heated air to enable the user to inhale the aromatic ingredients of the tobacco without inhaling the carcinogenic ingredients.

SUMMARY OF THE INVENTION

One aspect of this invention comprises a smokeless pipe for the ingestion of tobacco products. The pipe comprises an elongated hollow member having a proximal end, a distal end, and a length therebetween. The elongated hollow member includes a constricted portion along its length to retain the tobacco products within the elongated hollow member. The pipe additional includes a first opening located at the proximal end to enable a user to draw from the elongated hollow member, a fill port disposed along the length of the elongated hollow member to enable a user to fill the elongated hollow member with the tobacco products, and a bulbous chamber located at the distal end of the elongated hollow member, the bulbous chamber comprising at least one vent hole.

In other embodiments, the smokeless pipe is comprised of a two-piece apparatus. The first hollow member has an opening at its proximal end and at least one vent hole at its distal end. The second hollow member comprises an opening at its proximal end and at least one vent hole at its distal end.

Variations of this two-piece apparatus include the first hollow member comprising a constructed passageway exposed at its distal end. Also, the second hollow member includes a constricted passageway at its distal end. Furthermore, the two-piece apparatus can be interchanged to include one member having a constricted passageway and the other not having one.

In another embodiment of the two-piece apparatus, the second hollow member has an opening at its distal end to enable smoking material to be packed inside the inner chamber.

It yet another embodiment, the smokeless pipe comprises a three piece apparatus. The first hollow member comprises an opening at its proximal end and at least one vent hole at its distal end. The second hollow member comprises an opening at both the proximal and distal ends. The distal end opening is arranged to have smoking materials packed inside the inner chamber. The third hollow member is identical to the first hollow member but is smaller in diameter.

DETAILED DESCRIPTION OF THE PREFERRED EMBODIMENT

Figure 1:
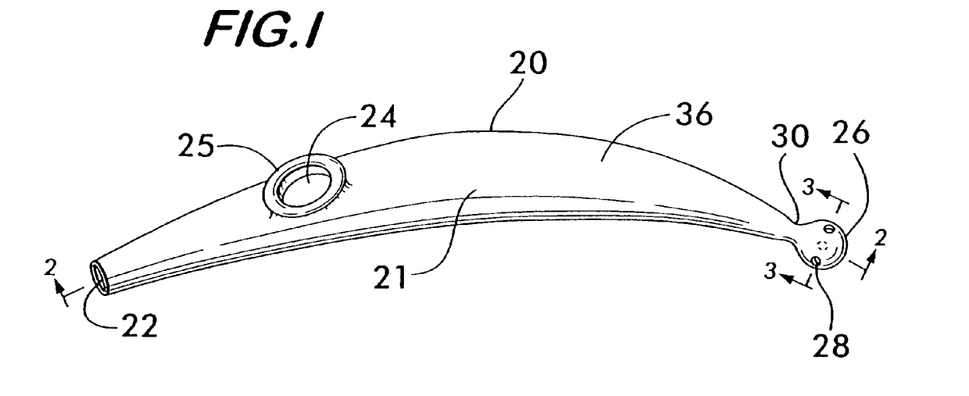
FIG. 1 is an isometric view of the preferred embodiment of a smokeless pipe constructed in accordance with the subject invention.

Referring now to the various figures of the drawings wherein like reference characters refer to like parts there is shown in FIG. 1 a smokeless pipe 20 constructed in accordance with this invention.

The smokeless pipe 20 is shown comprising an elongated hollow member 21 and a first opening 22 at the proximal end which enables a user to draw from the hollow member 21. Located at the most distal end of the hollow member is a bulbous chamber 26 which includes at least one vent hole 28 disposed along the circumference of the bulbous chamber 26. The bulbous chamber 26 is a multiple intake chamber that allows a heat/air mixture to generate inside the bulbous chamber 26. It should be understood that the bulbous chamber is not limited to any particular shape or size. Moreover, the bulbous chamber can include a plurality of vent holes 28 to accomplish the heat/air mixing.

The preferred embodiment in FIG. 1 is shown comprising three vent holes 28. It should be understood that the bulbous chamber 26 is not limited to just three vent holes 28. Whereas the bulbous chamber can include any amount of vent holes that is consistent with the scope of the invention.

It should be pointed out at this juncture that the smokeless pipe 20 is preferably made of glass. However, the smokeless pipe can be constructed of any material that is rigid and has a low heat index, e.g., ceramic.

Disposed along the length of the smokeless pipe is a fill port 24. The fill port 24 enables a user of to fill the smokeless pipe with smoking materials. It should be pointed out at this juncture that term "smoking materials" is intended to include any combustible organic material containing volatile ingredients which upon combustion are vaporized and can be drawn into the mouth and respiratory passages of a user, e.g., tobacco, licorice, eucalyptus, teas, flower petals, and other herbs.

Disposed along the distal end is a constricted passageway 30. The constricted passageway 30 prevents the smoking materials from entering into the bulbous chamber 26.

Figure 2:
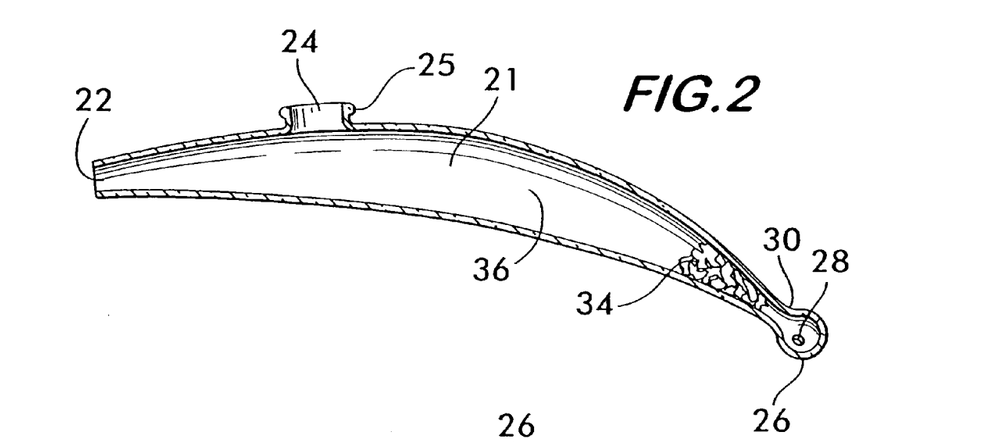
FIG. 2 is a sectional view taken along line 2-2 of FIG. 1, shown with tobacco product located inside the hollow member.

Referring now to FIG. 2 there is shown a sectional view taken along line 2-2 of FIG. 1. The smokeless pipe 20 is shown with smoking materials 34 located inside the hollow chamber 36. As shown in FIG. 2, the smoking materials 34 are collected towards the distal portion of the hollow chamber 36. The constricted passageway 30 avoids any of the smoking materials from entering the bulbous chamber 26.

Once the smoking materials are placed inside the pipe, a user would utilize a conventional lighter to add heat to the bulbous chamber. This is done by holding the flame so that the non-combustible portion of the flame adds heat inside the bulbous chamber 26. A combination of the heat added by the flame and an air-stream being brought in through the vent holes 28 by a user's inhaling at the first opening 22, enable the smoking materials to be warmed without combustion taking place. Thus, a user will be able to inhale the active volatile compounds and components of tobacco and of other smoking materials without the ingestion of toxic and carcinogenic compounds.

Referring again to FIG. 2, the fill port 24 forms ring 25 raised above the length of the elongated hollow member 21. The ring 25 allows the user to fill the smokeless pipe with ease and avoid any clogging of the smoking materials inside the hollow chamber 36. Furthermore, when the user wishes to rid the hollow chamber 36 of smoking materials, the large diameter of the ring allows the smoking materials to fall out of the smokeless pipe conveniently.

Figure 3:
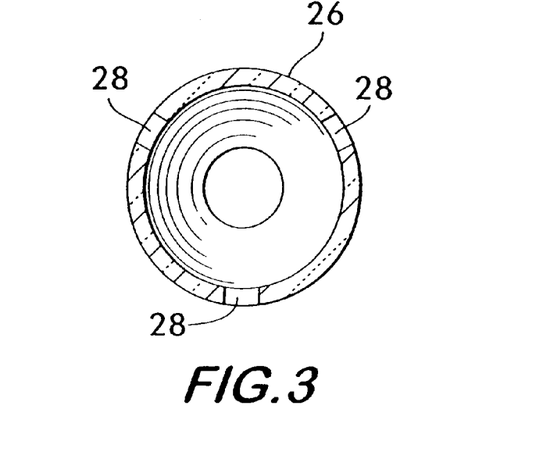
FIG. 3 is an enlarged sectional view taken along line 3-3 of FIG. 1.

Referring now to FIG. 3 there is shown a sectional view taken along line 3-3 of FIG. 1. The bulbous chamber 26 is shown comprising three vent holes 28 spaced equidistantly about the circumference of the bulbous chamber 26. However, it should be noted that the vent holes can be spaced at any distance from one another.

Figures 4, 5:
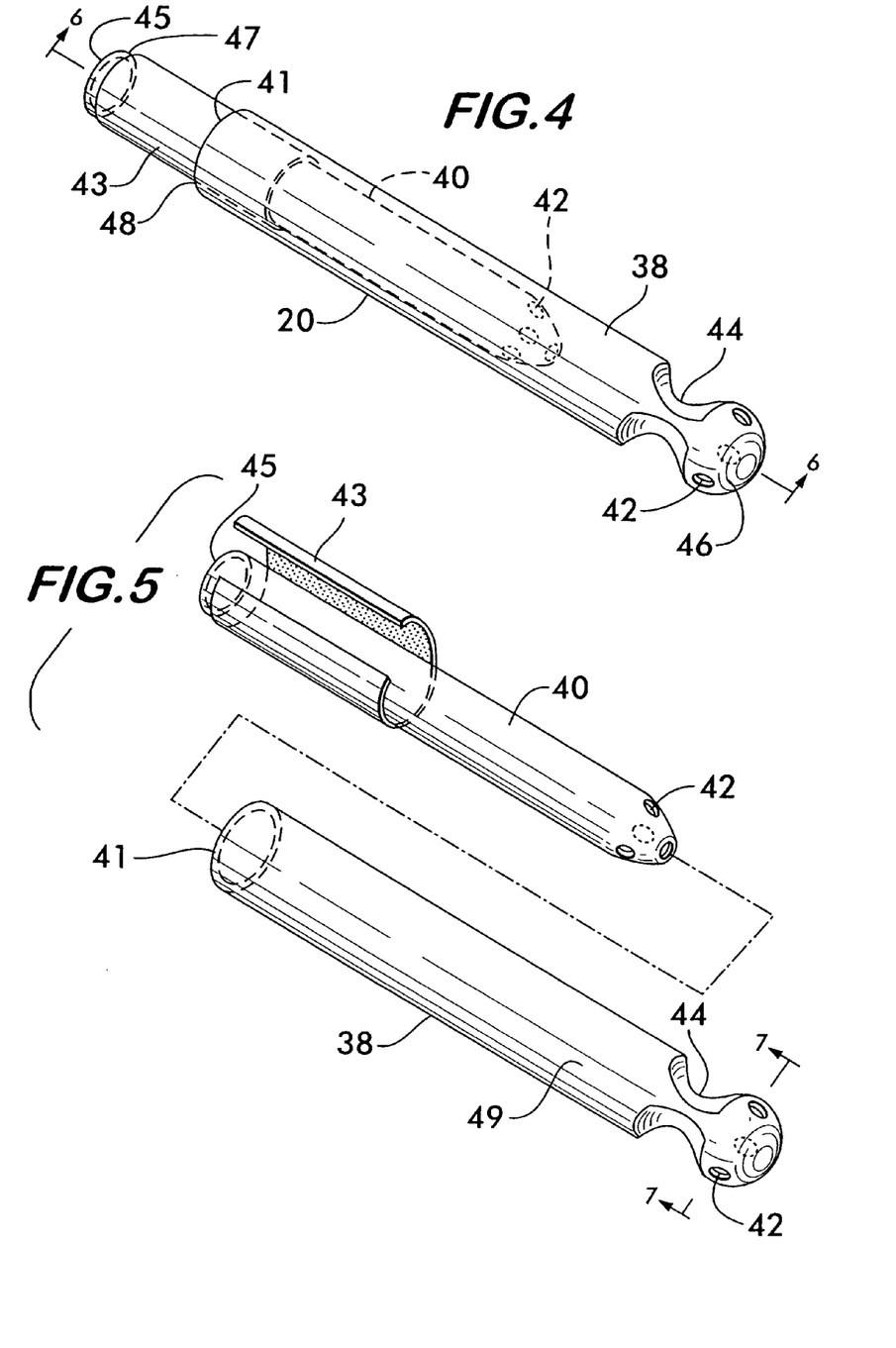
FIG. 4 is an isometric view of a second exemplary embodiment of an apparatus for a smokeless pipe constructed in accordance with the subject invention shown with a second hollow member placed inside a first hollow member, and the first hollow member is shown comprising a constricted passageway.
FIG. 5 is an isometric view of the second exemplary embodiment shown with the second hollow member placed outside the first hollow member.

Referring now to FIG. 4 there is shown a second exemplary embodiment of an apparatus for a smokeless pipe constructed in accordance with the subject invention. The smokeless pipe in FIG. 4 comprises a first hollow member 38 and a second hollow member 40. The first hollow member 38 has an opening 41 at its proximal end and at least one vent hole 42 at its distal end. The first hollow member further comprises a constricted passageway 44 which restricts any smoking materials from entering the bulbous chamber 46. It should be understood that the term "constricted passageway" includes any portion of the hollow member that restricts material from passing through the hollow member. Moreover, the various embodiments of this invention are not limited to one constricted passageway 44. The first hollow member is adapted to have the second hollow member 40 placed therein.

The second hollow member 40 comprises an opening 45 at its proximal end and at least one vent hole 42 at its distal end. The second hollow member further comprises a retention bearing 43 disposed over the outer surface 47 of the second hollow member 40. The retention bearing 43 is arranged to engage the inner surface 48 of the first hollow member 38 to retain the second hollow member 40 within the first hollow member 38.

Figure 8:
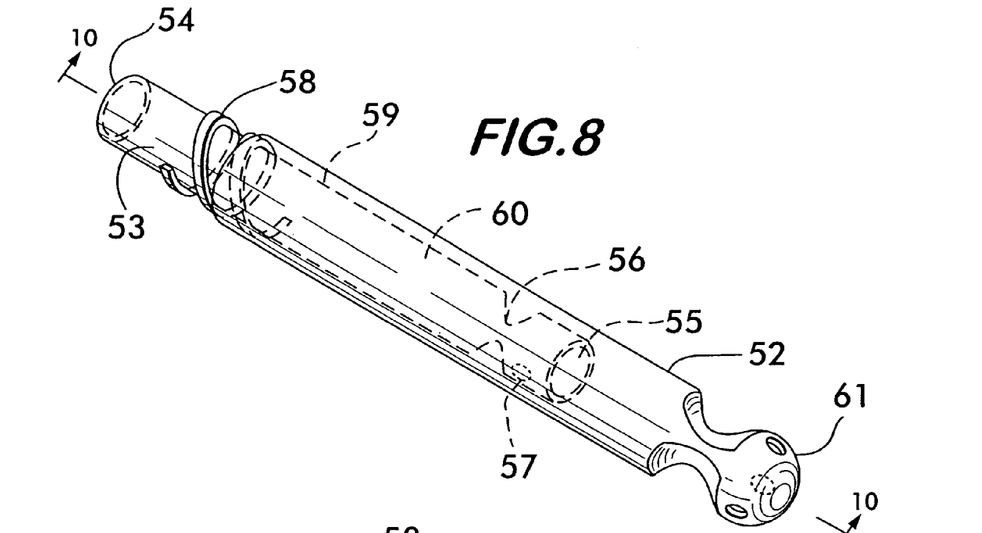
FIG. 8 is an isometric view of a third exemplary embodiment of an apparatus for a smokeless pipe constructed in accordance with the subject invention shown with the second hollow member placed inside the first hollow member, the second hollow member comprising a constricted passageway.

It should be understood that the retention bearing 43 is not limited to the style and shape shown in FIG. 4. As will be seen in further embodiments, the retention bearing 43 can vary in length and shape, e.g., a solid piece wrapping all the way around the hollow member or a thin strip wrapped helically one revolution around the hollow member (FIG. 8).

Furthermore, the retention bearing 43 is made of a flexible, rigid material that has an inner surface that can be affixed to the second hollow member, e.g., adhesive or glue.

Referring now to FIG. 5 there is shown the embodiment of FIG. 4 with the second hollow member 40 exposed outside the first hollow member 38. Prior to interlocking the two members, a user would fill the inner chamber 49 through the opening 41 of the first hollow member 38 with smoking materials. The smoking materials would fall down towards the restricted passageway 44 and collect inside the inner chamber 49 (see FIG. 6).

Once the smoking material is in place, the user then would place the second hollow member 40 inside the first hollow member 38 (FIG. 4). Once the retention bearing 43 engages the two members together, the smokeless pipe is ready to be used as described in the first embodiment above.

After such use, the user can take the second hollow member 40 out of the first hollow member 38 and allow the used smoking materials to fall out of the inner chamber.

Figure 6:
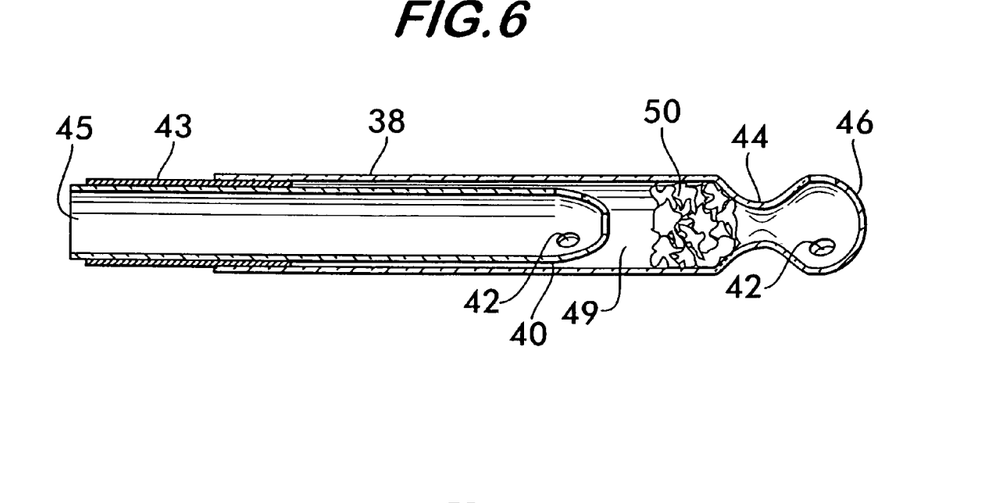
FIG. 6 is a sectional view taken along line 6-6 of FIG. 4 shown with tobacco product located in the first hollow member.

Referring now to FIG. 6 there is shown a cross sectional view taken along line 6-6 of FIG. 4. As described above, the smoking materials 50 are shown collected inside the inner chamber 49 of the first hollow member 38. The constricted passageway is narrow enough to prevent any smoking materials 50 from either entering the bulbous chamber 46.

When a user places the second hollow member 40 inside the first hollow member 38, the retention bearing engages the two members so that the second hollow member 40 does not come into contact with the smoking materials.

The second hollow member 40 comprises a vent hole 42 at its distal end. Thus, when a user draws from the opening 45 of the second hollow member 40, the active volatile compounds and components of the smoking material travels from the inner chamber 49 of the first hollow member 38 through the vent hole(s) 42, and out the opening 45 of the second hollow member 40.

Figure 7:
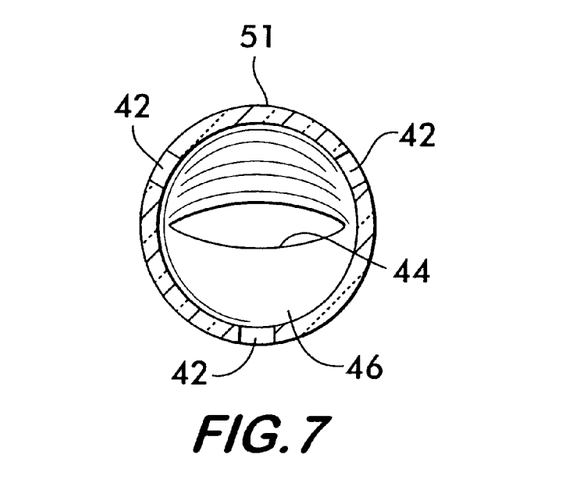
FIG. 7 is an enlarged sectional view taken along line 7-7 of FIG. 5.

Referring now to FIG. 7 there is shown a cross sectional view taken along line 7-7 of FIG. 5. The vent holes 42 are shown to be spaces equidistantly around the circumference 51 of the bulbous chamber 46 although the invention does not require and is not limited to equidistant spacing. The constricted passageway 44 is shown to be shaped narrowly in the form of an eye. Thus, it is visually appreciated that the constriction will avoid the smoking materials from entering the bulbous chamber 46.

Referring now to FIG. 8 there is shown another embodiment of the invention. The first hollow member 52 is identical to the first hollow member 38 of FIG. 4. However, the second hollow member 53 comprises an opening 54 at its proximal end and an opening 55 at its distal end. Furthermore, the second hollow member 53 comprises a constricted passageway 56 at its distal end and a blow hole 57.

Arranged around the proximal end of the second hollow member 53 is a retention bearing 58 which is wrapped around the proximal end of the second open end 53 approximately one revolution. The outer surface of the retention bearing engages the inner surface 59 of the first hollow member 52.

The opening 55 at the distal end is arranged to be filled with smoking materials. In this embodiment, the opening 55 acts as a fill port whereby the smoking materials are packed inside the chamber. The constricted passageway 56 prevents the smoking materials from entering into the inner chamber 60 of the second hollow member 53.

As explained above, the retention bearing 58 will allow insertion of the second hollow member 53 far enough into the first hollow member 52 so that the smoking materials are not combusted when heat is added to the bulbous chamber 61. When heat is added to the bulbous chamber 61, the user will draw from the opening 54 of the second hollow member 53. The active volatile compounds and components of the smoking material travel from the smoking materials, through the constricted passageway 56, and out through the opening 54 of the second hollow member 53.

When the user is finished utilizing the smokeless pipe, he can rid the smoking materials out of the opening at the distal end (see FIG. 10) by blowing air through the blow hole 57. An alternative method could be utilized by simply tapping the second hollow member 53 against a surface. However, to avoid destruction to the outer surface, blowing through the blow hole 57 is preferred.

Figure 9:
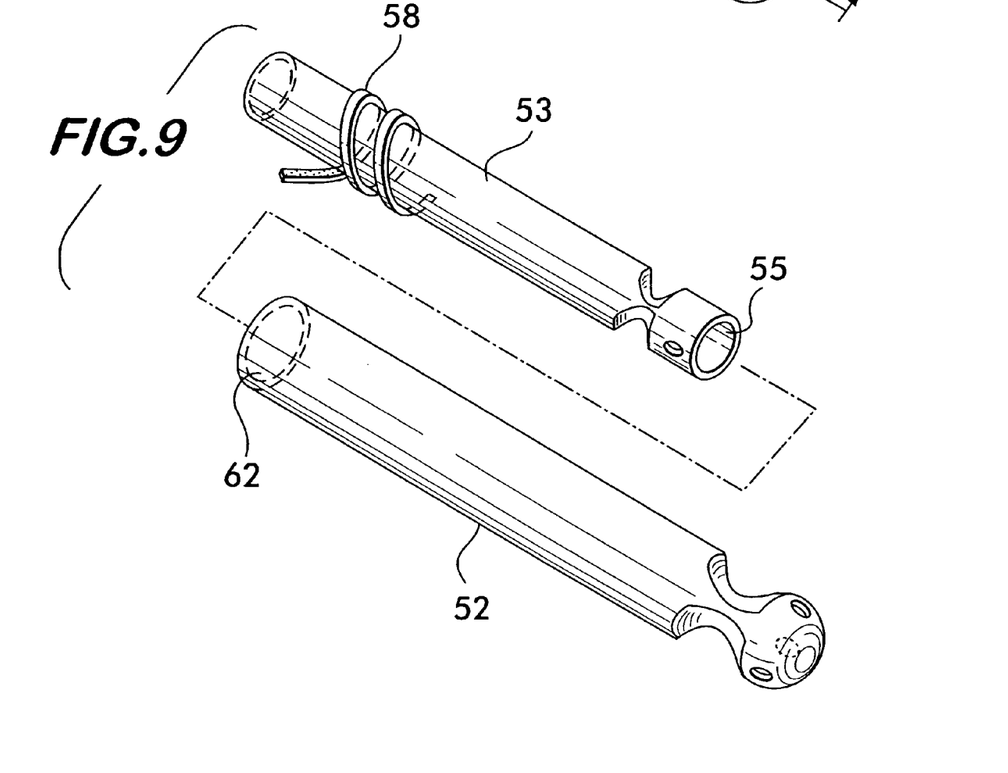
FIG. 9 is an isometric view of the third exemplary embodiment of an apparatus for a smokeless pipe constructed in accordance with the subject invention shown with the second hollow member placed outside the first hollow member.

Referring now to FIG. 9 there is shown the embodiment of FIG. 8 where the second hollow member 53 is placed outside of the first hollow member 52. It can be visually appreciated that the opening 62 of the first hollow member 52 has a diameter greater than the diameter of the opening of the second hollow member. This enables the two members to be nested within one another so that the retention bearing 58 will determine the point of engagement.

Figure 10:
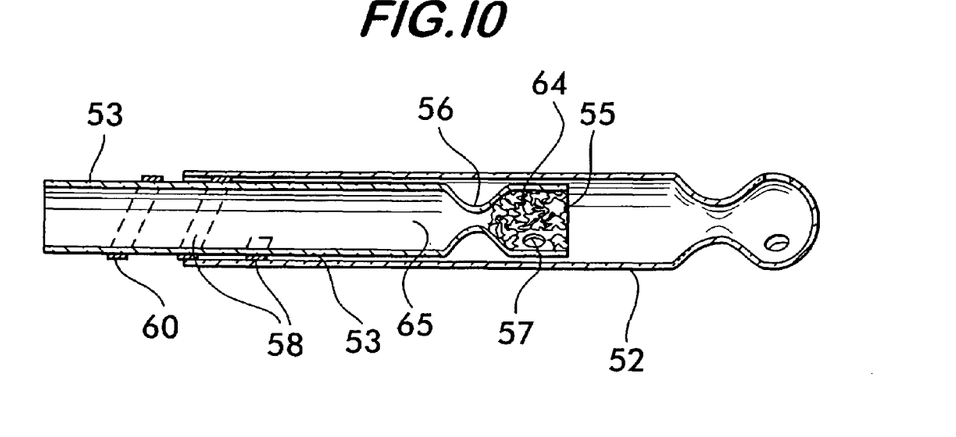
FIG. 10 is a sectional view taken along line 10-10 of FIG. 8 shown with tobacco product located inside the first hollow member.

Referring now to FIG. 10 which is a cross sectional view taken along line 10-10 of FIG. 8, there is shown the opening 55 of the second hollow member 53 packed with the smoking material 64 collected therein. The constricted passageway 56 restricts the smoking materials from entering into the inner chamber 65 of the second hollow member. This embodiment utilizes a narrow strip retention bearing 58. As shown in FIG. 10, the inner surface 57 of the first hollow member 52 becomes engaged with the outer surface 60 of the retention bearing 58. The outer surface 60 of the retention bearing 58 is comprised of a material that will not adhere to the inner surface 57 of the first hollow member 52. Moreover, the outer surface 60 of the retention bearing 58 will frictionally engage the inner surface of the first hollow member 52 so that the distance the second hollow member 53 is placed inside the first hollow member 52 can vary.

Figure 11:
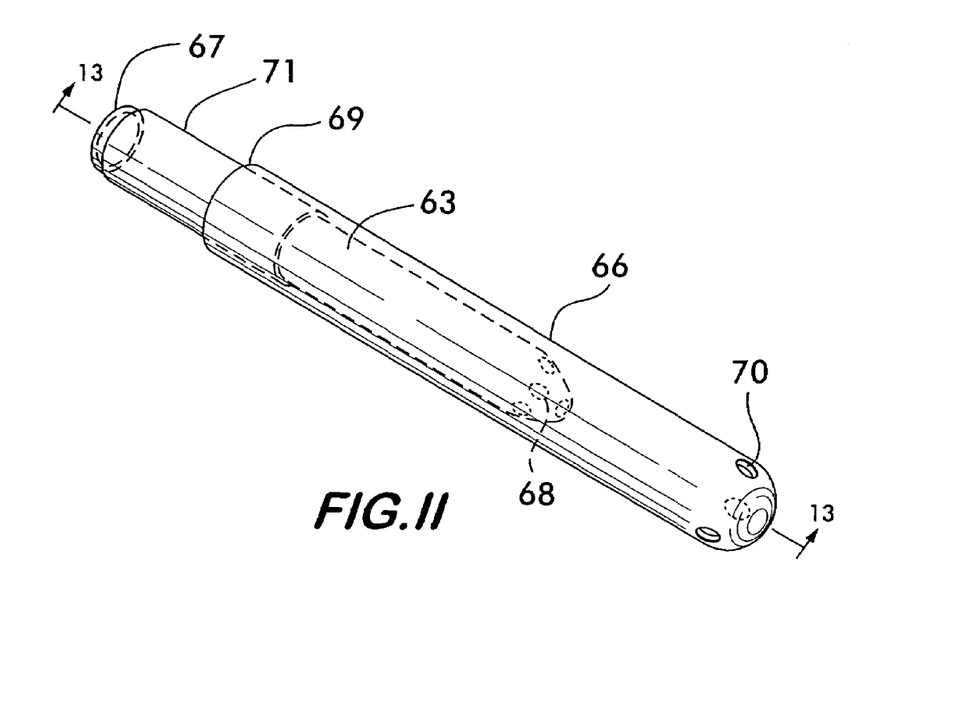
FIG. 11 is an isometric view of a fourth exemplary embodiment of an apparatus for a smokeless pipe constructed in accordance with the subject invention shown with the second hollow member placed inside the first hollow member, and the second hollow member shown without a constricted passageway.

Referring now to FIG. 11 there is shown another embodiment of the invention. The first hollow member 66 has an opening 69 at its proximal end and at least one vent hole 70 at its distal end. The second hollow member 63 has an opening 67 at its proximal end and at least one vent hole 68 at its distal end. Furthermore, the second hollow member 63 comprises a retention bearing disposed over its outer surface. The primary difference with that of the embodiment shown in FIG. 11 as compared to the other embodiments described above is that the embodiment in FIG. 11 contains no constricted passageway.

Figure 13:
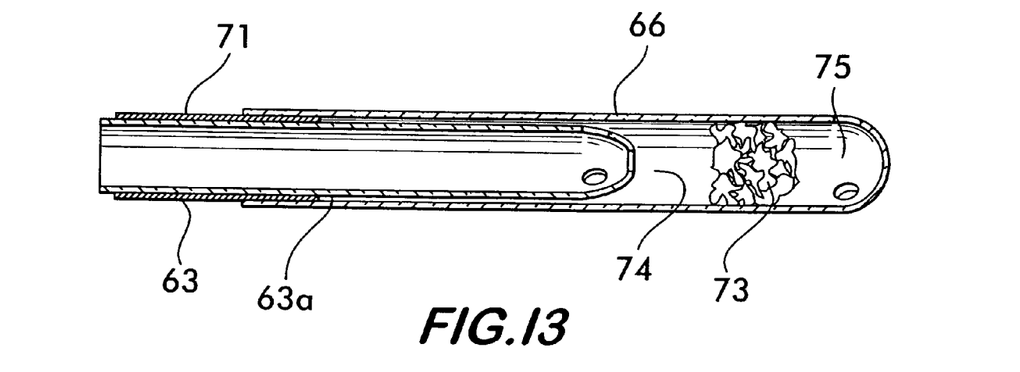
FIG. 13 is a sectional view taken along line 13-13 of FIG. 11 shown with tobacco product located inside the first hollow member.

However, the first hollow member 66 comprises a plurality of vent holes 70 about the circumference of the distal end. The second hollow member also includes a plurality of vent holes exposed along the circumference of its distal end. The smoking materials are placed inside the inner chamber of the first hollow member (FIG. 13). The second hollow member 63 is placed inside the first hollow member 66. The retention bearing 71 enables the two hollow members (63,66) to nest and frictionally engage prior to the retention bearing 71 with the inner surface 63a of the first hollow member 66.

Figure 12:
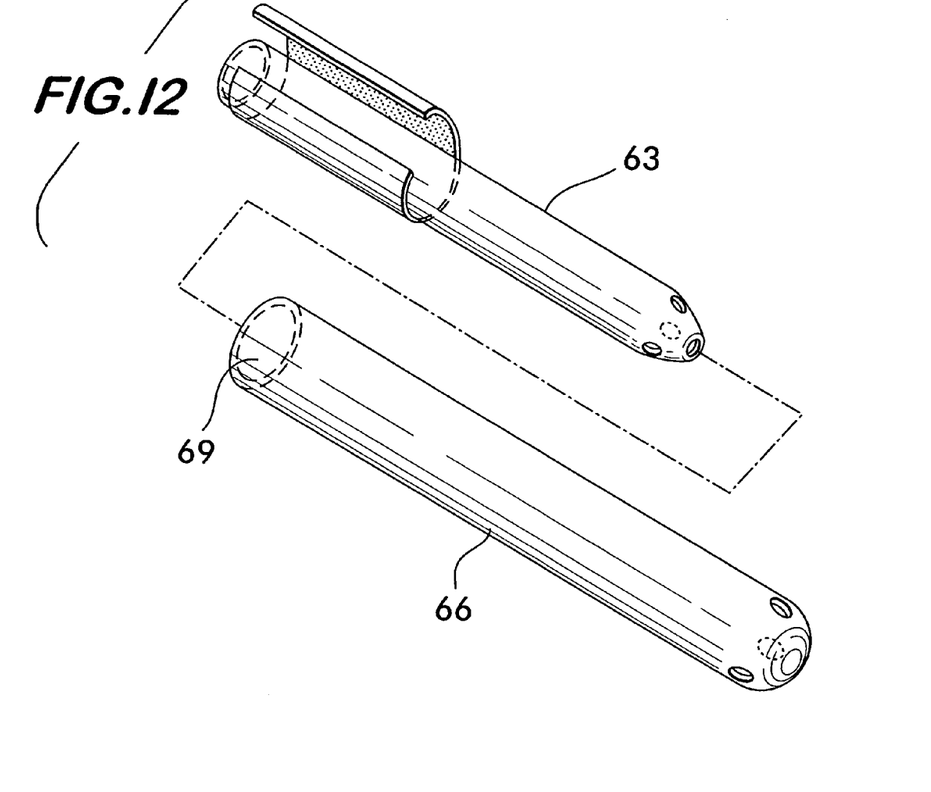
FIG. 12 is an isometric view of the fourth exemplary embodiment of an apparatus for a smokeless pipe constructed in accordance with the subject invention shown with the second hollow member placed outside the first hollow member.

Referring now to FIG. 12 there is shown the embodiment of FIG. 11 with the second hollow member 63 placed outside the first hollow member 66. FIG. 13, which is a cross sectional view taken along line 13-13 of FIG. 1, shows the same embodiment with the two members (63,66) nested within one another and frictionally engaged with the smoking material 73 placed inside the inner chamber 74 of the first hollow member 66.

In order to utilize the embodiment of FIGS. 11-13, the user has to hold the smokeless pipe so that the smoking material 73 does not fall to the distal end 75 of the first hollow member 66. The user can first fill the first hollow member through the opening 69 with enough smoking material 73 that allow it to collect. Once accomplished, the collected smoking material 73 can be guided along the length of the first hollow member with any suitable object so that the smoking material 73 becomes lodged at a certain point inside the inner chamber 74 of the first hollow member 66.

Figure 14:
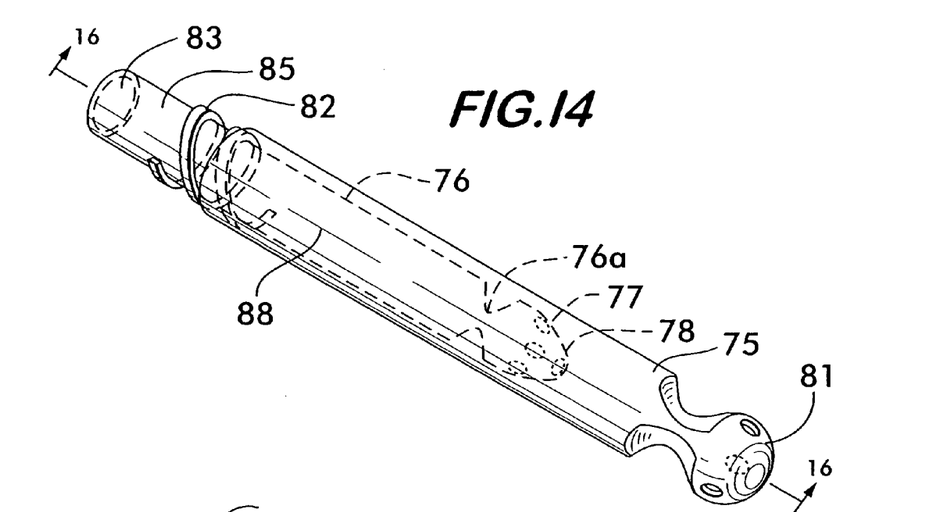
FIG. 14 is an isometric view of a fifth exemplary embodiment of an apparatus for a smokeless pipe constructed in accordance with the subject invention shown with the second hollow member placed inside the first hollow member, the second hollow member comprising a constricted passageway.

Referring now to FIG. 14, there is shown another embodiment of the smokeless pipe. This embodiment is another two-piece construction comprising a first hollow member 75 and a second hollow member 76. The first hollow member is the same as the first hollow member 52 shown and described in FIG. 8. However, the second hollow member comprises a restricted passageway 76a at its distal end and a plurality of vent holes 77 about the circumference of a bulbous chamber 81.

Figure 15:
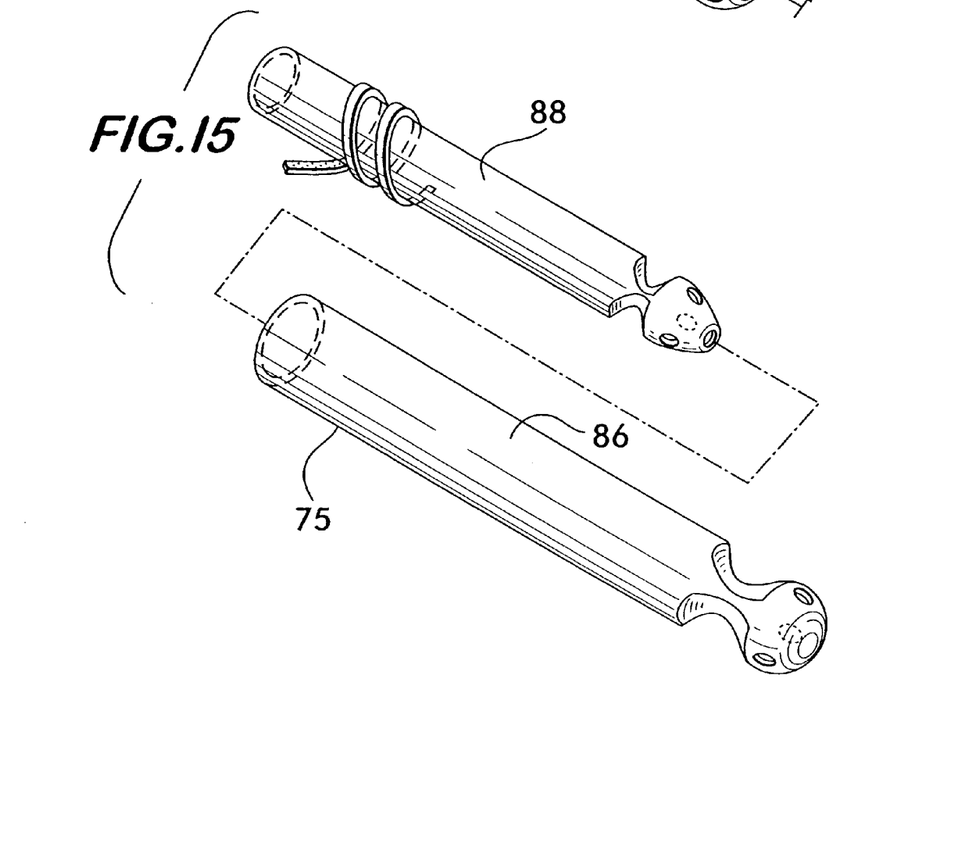
FIG. 15 is an isometric view of the fifth exemplary embodiment of an apparatus for a smokeless pipe constructed in accordance with the subject invention shown with the second hollow member placed outside the first hollow member.
Figure 16:
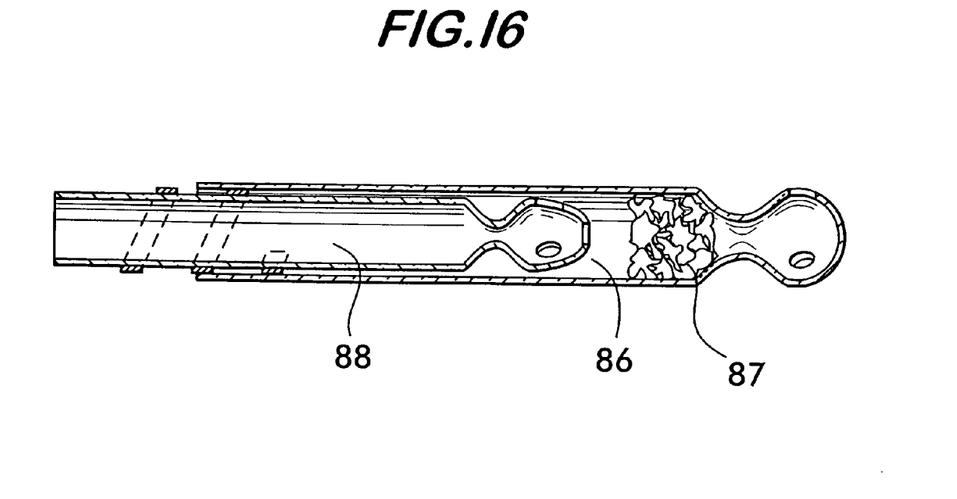
FIG. 16 is a sectional view taken along line 16-16 of FIG. 14 shown with tobacco product located inside the first hollow member.

Arranged around the proximal end 85 of the second hollow member 76 is a narrow strip retention bearing 82. The two-piece apparatus is arranged to have the second hollow member 76 placed inside the first hollow member 75. FIG. 15 shows the two-piece apparatus prior to placing the smoking material inside the inner chamber 86 of the first hollow member 75. FIG. 16, which is a cross sectional view taken along line 16-16 of FIG. 14, shows the embodiment with the smoking material placed inside the inner chamber 86 of the first hollow member.

The embodiment of FIGS. 14-16 functions in the same way as the previously described two-piece embodiments. The user draws from the open end 83 of the second hollow member 76 while adding heat to the bulbous chamber 81 of the first hollow member 75. Once the smoking material 87 is warmed enough to release the non-carcinogenic flavors, the components travel through the vent holes 77 of the second hollow member 76, and through the inner chamber 88 of the second hollow member. Finally, the components flow through the opening 83 into the users mouth.

Figure 17:
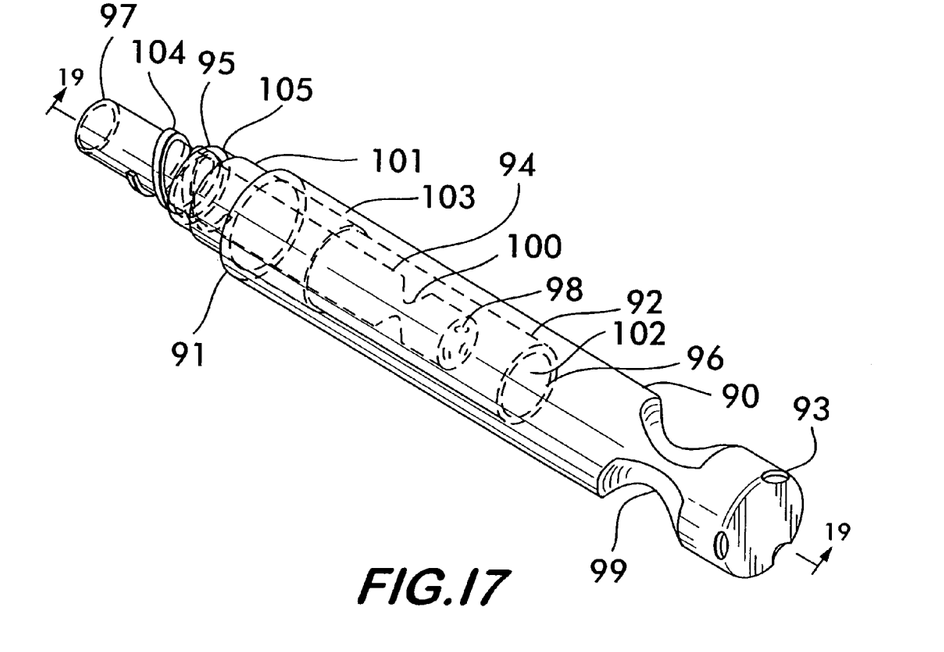
FIG. 17 is an isometric view of a sixth exemplary embodiment of an apparatus for a smokeless pipe constructed in accordance with the subject invention shown with a third hollow member placed inside a second hollow member, and the second hollow shown placed inside the first hollow member.
Figure 18:
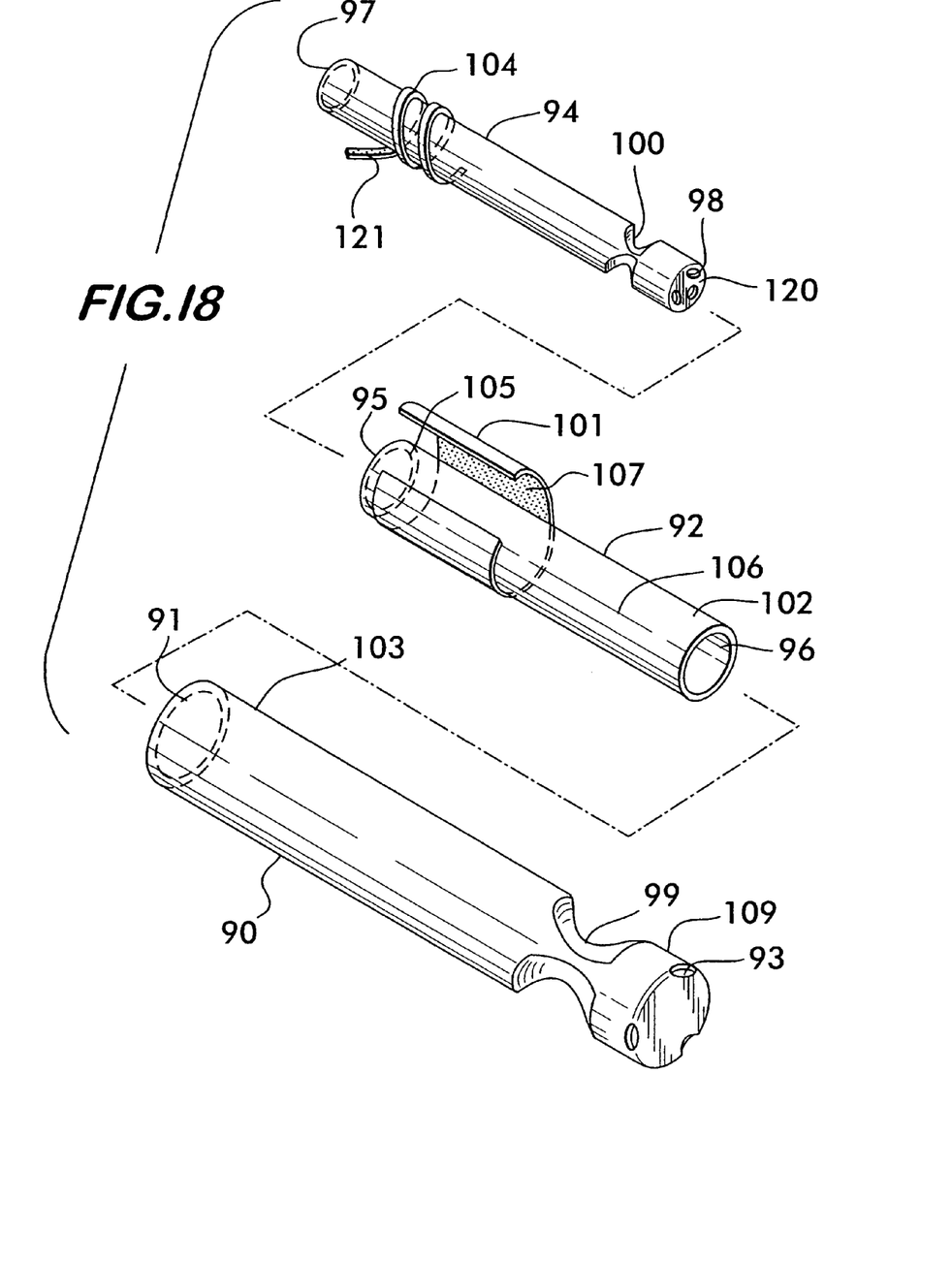
FIG. 18 is an isometric view of a seventh exemplary embodiment of an apparatus for a smokeless pipe constructed in accordance with the subject invention shown with the third hollow member placed outside the second hollow member, and with the second hollow member placed outside the first hollow member.
Figure 19:
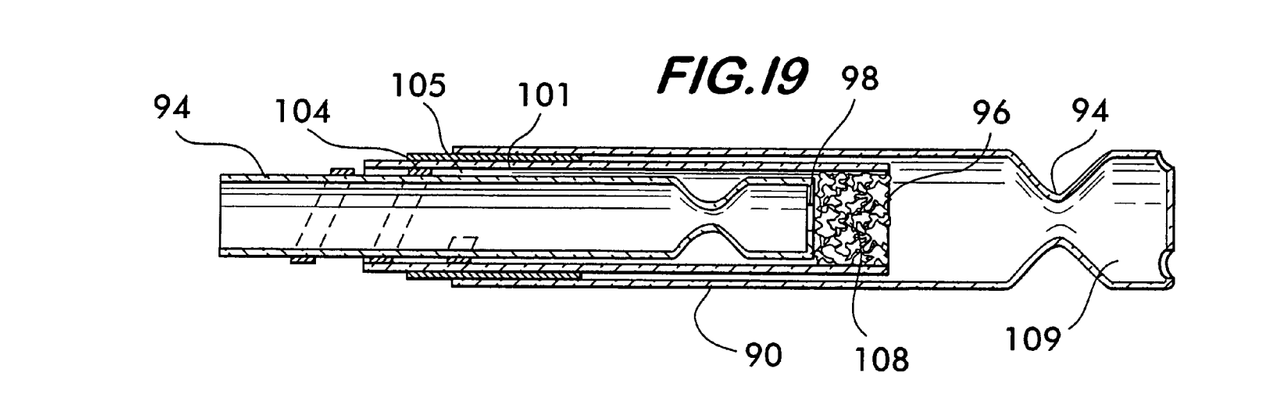
FIG. 19 is a sectional view taken along line 19-19 of FIG. 17 shown with tobacco product located inside the first hollow member.

Referring now to FIGS. 17,18 and 19, there is shown yet another embodiment of the smokeless pipe. Referring to FIG. 17, there is shown a three-piece apparatus. The first hollow member 90 comprises an opening 91 at its proximal end and at least one vent hole 93 at its distal end. Furthermore, the first hollow member 90 comprises a retention bearing 99 exposed along its length.

Attention is now directed to FIG. 18 wherein the second hollow member comprises an opening 95 at its proximal end and an opening 96 at its distal end. The opening 96 at the distal end is arranged to have smoking material packed inside the inner chamber 102 of the open end 96. The second hollow member 92 further comprises a retention bearing 101 adhered to the outside surface at the proximal end of the second hollow member 92. The retention bearing is adapted to come into contact with the inner surface 103 of the first hollow member 90.

The third hollow member 94 comprises an opening 97 at its proximal end and at least one vent hole 98 at its distal end. The third hollow member further includes a restricted passageway 100 and a retention bearing 104 applied to the outer surface at the proximal end of the third hollow member. The retention bearing 104 comes into contact with the inner surface 105 of the second hollow member 92.

If a user wishes to rid the smoking material from the inner chamber 102 of the second hollow member 92, he can use the closed end 120 of the third hollow member 94 to poke the smoking material out. This is done by sliding the third hollow member 94 far enough through the second hollow member 92 until the closed end 120 forces the smoking material out.

Referring again to FIG. 18, there is shown the three piece embodiment of FIG. 17 with each member shown separately. As can be appreciated, the first hollow member 90 is identical in configuration to but somewhat larger in size than the third hollow member 94. The third hollow member 94 has a diameter smaller than that of the first hollow member 90.

The second hollow member 92 has a continuous diameter 106 throughout its length. The second hollow member 92 is shown with a solid strip retention bearing 101 exposed around its proximal end. The inner surface 107 of the retention bearing is comprised of an adhesive material to be affixed to the second hollow member 92.

The third hollow member 94 has a narrow strip retention bearing 104 exposed around its proximal end. The inner surface 121 of the retention bearing also includes an adhesive material to be affixed to the third hollow member 94.

FIG. 19, which is a cross sectional view taken along line 19-19 of FIG. 17, shows the three piece embodiment with each member in its respective position. The smoking material 108 is collected inside the open end 96 of the second hollow member 92. Once the smoking material 108 is collected therein, the third hollow member 94 is placed inside the second hollow member 92. The retention bearing 104 comes into contact with the inner surface 105 of the second hollow member. Thus, the distal end of the third hollow member 94 is slid inside just enough so that the smoking material is adjacent the vent holes 98 of the third hollow member.

The second hollow member 92, with the third hollow member 94 placed therein, is then placed inside the first hollow member 90. The retention bearing 101 comes into contact with the inner surface 103 of the first hollow member. The opening 96 of the second hollow member 92 containing the smoking material 108 can be slid proximally or distally as far as the user wishes because the retention bearing 101 of the first hollow member 90 will avoid any smoking material 108 from entering the bulbous chamber 109.

Once all the members are in place as shown in FIG. 19, the active volatile compounds and components of the smoking material is released through the vent holes 98 of the third hollow member 94 and out through the opening 97 of the third hollow member 94 into a users mouth.

Figure 20:
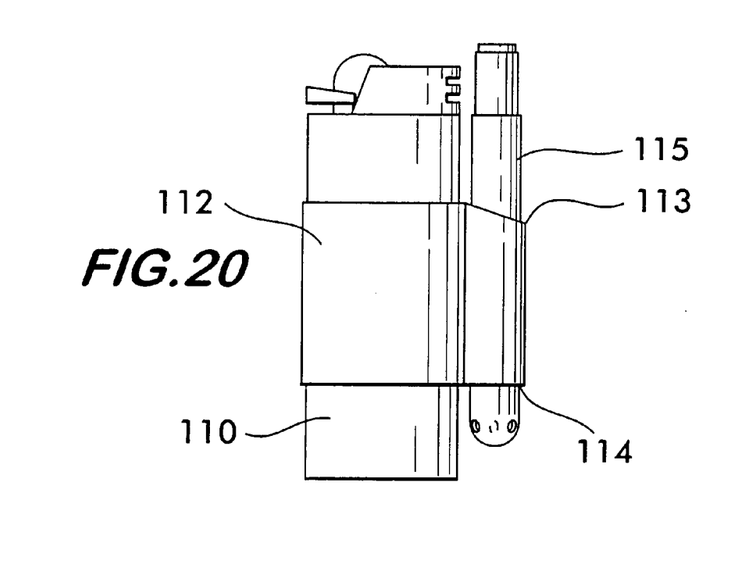
FIG. 20 is a side elevational view of one preferred embodiment of a sleeve for the storage of a smoking apparatus, shown with a smokeless pipe apparatus contained within the sleeve.

Referring now to FIG. 20 which is a side elevational view of one preferred embodiment of a sleeve for the storage of a smoking apparatus, shown with a smokeless pipe apparatus contained within the sleeve.

The sleeve 112 is comprised of a first open end 113 and a second open end 114 which enables a smoking apparatus 115 to be placed inside the sleeve 112. The sleeve is preferably made of a flexible, heat resistant material that can expand and compress to allow a tight fit, e.g., plastic or rubber. It should also be understood that the sleeve will be able to withstand a smoking apparatus that has been used and is hot. Moreover, the sleeve is not limited to having two open ends (113, 114). For example, the sleeve could have one closed end and one open end.

The sleeve 112 is attached to a conventional lighter 110 so that when the user is utilizing the smoking apparatus, the sleeve will not become detached. It should be pointed out at this juncture that the term "smoking apparatus" included any apparatus that is used for the ingestion of smoking materials, e.g., cigarettes, cigars, or smokeless pipes.

The first open end 113 and the second open end 114 are not limited to a certain diameter. The diameters can vary in range to accompany any smoking apparatus. However, the use of a flexible material will allow several different diameter smoking apparatus to be used with the same sleeve.

Figure 21:
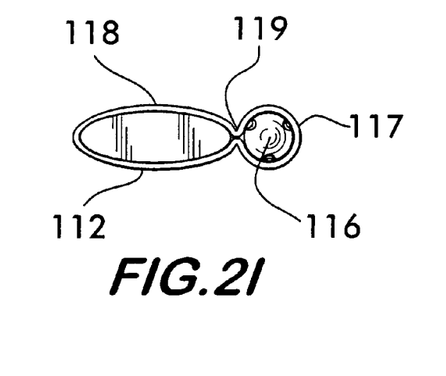
FIG. 21 is a bottom view of FIG. 20.

FIG. 21 which is a bottom view of FIG. 20, shows the nose 116 of a smoking apparatus 117 placed inside the sleeve. The circumference 118 of the sleeve wraps fully around the conventional light. It should be understood that the term "conventional lighter" includes any lighter that is suitable to ignite a smoking apparatus, e.g., butane gas or electric heat.

The neck 119 of the sleeve 112 forms a two-ply interlocking system that strengthens the overall support for the smoking apparatus 117 when placed inside the sleeve. Moreover the advantage of utilizing a flexible material that can be compressed is that the smoking apparatus 117 will not fall through the sleeve once contained therein.

Without further elaboration the foregoing will so fully illustrate our invention that others may, by applying current or future knowledge, adopt the same for use under various conditions of service.

What is claimed is:

1. An apparatus for the ingestion of non-combustible tobacco products, said apparatus comprising:
    a first hollow member comprising a first opening at a proximal end, at least one vent hole at a distal end, and a length therebetween, said first hollow member further comprising a bulbous chamber located at the distal end, a constricted portion along its length to retain the tobacco products within said first hollow member;
    a second hollow member arranged for insertion within said first hollow member, said second hollow member comprising an open proximal portion, an open distal portion arranged for retaining the tobacco within said open distal portion, and a length therebetween; and
    a third hollow member arranged for insertion within said second hollow member comprising an opening at a proximal end, at least one vent hole at a distal end, and a length therebetween, said third hollow member further comprising a retention bearing disposed on said third hollow member being arranged to engage the inner surface of said second hollow member to retain said third hollow member within said second hollow member.

2. The apparatus of claim 1 wherein said retention bearing is cylindrical in shape.

3. The apparatus of claim 1 wherein said at least one vent hole in said first hollow member comprises a plurality of vent holes.

4. The apparatus of claim 3 wherein said plurality of vent holes are spaced equidistantly about said bulbous chamber.

5. The apparatus of claim 1 wherein said at least one vent hole in said third hollow member comprises a plurality of vent holes.

6. The apparatus of claim 5 wherein said plurality of vent holes are spaced equidistantly about said bulbous chamber.

7. An apparatus for the ingestion of non-combustible tobacco products, said apparatus comprising:
    a first hollow member comprising an opening at a proximal end and at least one vent hole at a distal end;
    a second hollow member arranged for insertion within said first hollow member, said second hollow member comprising an open proximal portion, an open distal portion and a constriction therebetween for retaining tobacco within said distal portion, said second hollow member further comprising a blow hole disposed on said distal portion; and
    a retention bearing disposed on said second hollow member being arranged to engage the inner surface of said first hollow member to retain said second hollow member within said first hollow member.

8. The apparatus of claim 7 wherein said retention bearing is cylindrical in shape.

9. An apparatus for the ingestion of non-combustible tobacco products, said apparatus comprising:
    a first hollow member comprising an opening at a proximal end, at least one vent hole at a distal end and a length therebetween;
    a second hollow member arranged for insertion within said first hollow member, said second hollow member comprising an opening at a proximal end, at least one vent hole at a distal end, and a length therebetween, said second hollow member further comprising a retention bearing disposed over the outer surface of said second hollow member, said retention bearing being arranged to engage the inner surface of said first hollow member to retain said second hollow member within said first hollow member; and,
    a bulbous chamber located at the distal end of said first hollow member, said first hollow member including a constricted portion along its length to retain the tobacco products within said first hollow member, said second hollow member additionally comprising a bulbous chamber and a constricted passageway at said distal end thereof.

* * * * *